United States Patent
Wiezenthal

Patent Number: 5,590,471
Date of Patent: Jan. 7, 1997

[54] BANDAGE CUTTER

[76] Inventor: Saul Wiezenthal, P. O. Box 440901, Miami, Fla. 33144

[21] Appl. No.: 555,603

[22] Filed: Nov. 9, 1995

[51] Int. Cl.$^6$ .................................................. B26B 29/02
[52] U.S. Cl. .................................... 30/294; 30/DIG. 3
[58] Field of Search .............................. 30/294, DIG. 3, 30/286, 280, 295, 314, 2

[56] References Cited

U.S. PATENT DOCUMENTS

| | | | |
|---|---|---|---|
| 2,610,399 | 9/1952 | Adams et al. | 30/294 X |
| 3,100,935 | 8/1963 | Leafe | 30/294 |
| 3,613,241 | 10/1971 | Allen | 30/294 |
| 3,751,806 | 8/1973 | Patrick | 30/294 |

*Primary Examiner*—Douglas D. Watts
*Attorney, Agent, or Firm*—John Cyril Malloy

[57] ABSTRACT

A bandage cutter which includes a short, thick, relatively blunt ended finger which extends in spaced generally parallel relation along one edge of a generally flat disk-shaped handle. The finger curves to a terminal end; and the finger defines a throat between it and the handle with an open mouth. Preferably, a thickened rim is provided about the throat protectively shielding the cutting edge of a blade spanning the throat. The blade of stainless steel presents a cutting edge at a slope of about 45° to the edge of a bandage. A curved rocker surface on the handle is provided to manipulate the cutter to a preferred cutting angle while a bandage is held taut for initiating a slicing action. The handle includes a bearing surface for pushing by the index finger of a user while simultaneously the handle is grasped between the thumb and middle finger, on opposite sides of the handle respectively, to orient the attitude of the cutter while slicing action takes place.

9 Claims, 1 Drawing Sheet

BANDAGE CUTTER

BACKGROUND AND SUMMARY OF THE INVENTION

This invention is of a bandage cutter to quickly, easily and rapidly remove a bandage from a wearer, whether a person or animal, such as about one's limb, without pulling and pushing forces being applied to the injured limb or protected area thereof.

The cutter at first blush is reminiscent of a letter opener in that it includes a handle with a finger, extending from one edge of the handle to the other in spaced relation therewith defining a throat which has a blade spanning it in a deep throat location presenting a slope of about 30° to the juncture of an envelope flap to the envelope body. In the case of a letter opener, once the finger, which is long and distally pointed, has been inserted deeply into the letter under the flap, the cutter is moved swiftly along the edge of the letter to slice it open. In use, the letter opener handle is grasped between the thumb of the user on one side and the index and center finger on the other side; and, while grasped in this manner, a generally slicing action takes place directed outwardly away from the user in a more or less sweeping outward and side-wise movement.

This bandage cutter invention includes a short, thick, blunt ended finger in spaced generally parallel relation along one edge of a generally flat handle. This structure defines a throat between the finger and the handle with an open mouth. A thickened rim is provided about the throat. The thickened rim protectively shields a user from contact with the cutting edge of a blade spanning the throat. The blade, preferably of stainless steel, presents a cutting edge at a slope of about 48° to the end of a bandage. A curved surface, called a rocker surface, is provided to manipulate and to hook the blunt end of the short finger to guide the cutter over the end of a sleeve configured bandage. Also, a thick bearing surface is provided to cradle the index finger of a user while applying a cutting force to slice a longitudinally extending opening in the bandage while the handle is being grasped between the thumb on one side of the handle, and the middle finger on the other side of the handle which orients the attitude of the cutter relative to the sleeve-type bandage. Preferably, the cutter is of molded plastic material in the rigid range. The blade includes a triangular shaped alignment hole so that the blade may be positioned and oriented relative to the cutter body while being molded.

In use, the curved rocker edge of the handle is positioned against the skin of a wearer of a bandage after the blunt end of the short finger has been inserted between the skin and the bandage as illustrated in the drawings. The bandage is kept taut; circumferentially as opposed to longitudinally. The more taut or tighter it is stretched, the easier it is to slice it open. The cutter is manipulated by swinging movement of it on its curved rocker surface until the correct angle is determined and/or adjusted. Thereafter, a longitudinally directed force is applied to the cutter preferably by the index finger, while the cutter is oriented by the thumb and middle finger, to slice a longitudinal opening in the bandage so that it can be peeled open and removed from about the limb of a wearer.

Examples of use of the cutter are to remove bandages from persons in an emergency room or treatment center and to remove wraps or bandages from the legs of horses.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
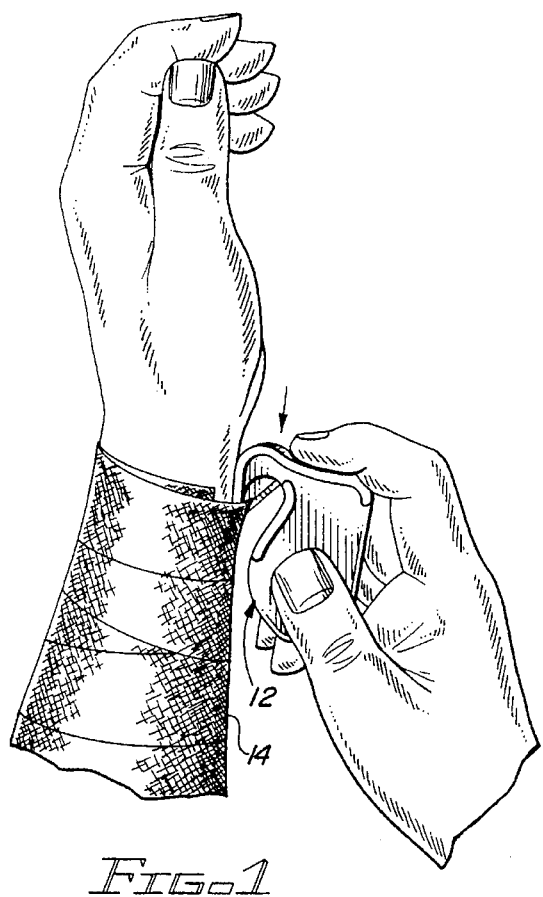
FIG. 1 is a perspective view of the bandage cutter in use.
Figure 2:
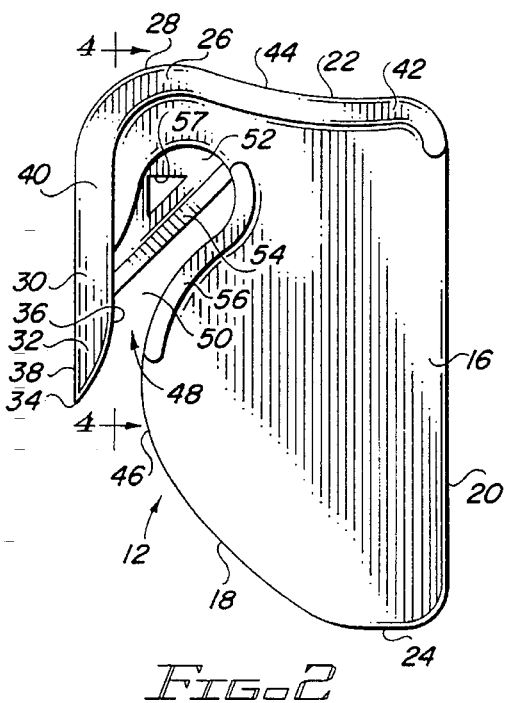
FIG. 2 is an elevation view of the cutter.
Figure 3:
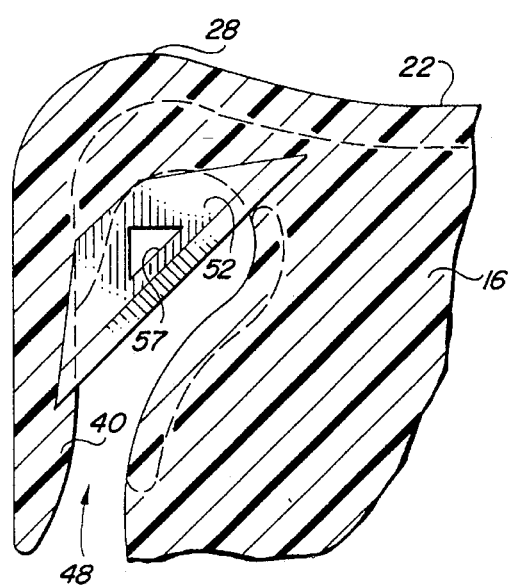
FIG. 3 is a partial view in cross section of the upper left hand portion of FIG. 2.
Figure 4:
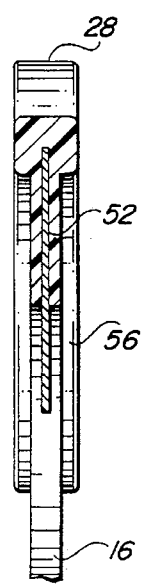
FIG. 4 is a partial view in cross section taken on the plane indicated by the arrowed line 4—4 of FIG. 2.

The invention includes a cutter generally designated by the numeral 12 which, as illustrated, is used to slice a longitudinally extending opening between the ends of a generally sleeve-shaped item 14, such as a bandage of flexible pliable material, while it remains in position about the limb of a wearer. The cutter provides for easy removal of the bandage, after the slit from end to end along the bandage has been made, by simply peeling the bandage apart along the opening.

The cutter includes a handle portion 16 with opposite, generally planar and parallel main surfaces which, in use, are gripped between the thumb and the middle finger of a user. The handle portion has a first edge surface 18, an opposite edge surface 20, a top bearing surface 22, and a bottom surface 24 with the distance between the top bearing surface and the bottom surface at its maximum dimension being between about 2½ inches and 3½ inches. The handle portion includes a connecting portion 26 which also has a top surface 28 and a relatively short guide finger 30 extending from the connecting portion. The finger as shown is disposed in spaced relation along a portion of the first edge surface. The finger has a distal end zone 32 with a terminal end 34, an inside surface 36 curving to the terminal end, and an outside surface 38, the inside surface 36 confronting the first edge surface. The finger also has spaced side surfaces such as that indicated by the numeral 40. The finger is symmetrical with the main faces of the handle portion; but it is thickened between the side surfaces with respect to the thickness of the handle portion, the thickness of the finger being between about 3/16 inch to ¼ inch while the length of the finger between the terminal end and the top bearing surface is about 1½ inches or about one-half of the overall distance between the bottom edge and the top bearing surface of the handle portion. As indicated, the top bearing surface 22 and the top surface 28 of the connecting portion 26 are symmetrical with respect to the handle portion and are provided with a thickened rim portion 42 with the side surfaces of the rim portion being conterminous with the side surfaces of the finger. The rim of the top bearing surface and the top surface of the connecting portion are curved somewhat defining a cradle 44 extending into the handle portion in a depth-wise direction generally parallel to the guide finger to accommodate a pushing force applied to the top bearing surface of the cutter by an index finger of a user. The first edge surface 18 of the cutter is curved upwardly from the bottom surface 24 to a crown 46 opposite to and in confronting relation to the distal end zone of the finger. This defines a curved guide surface for initially hooking up the cutter at the end/edge of a sleeve-shaped bandage; and it accommodates tilting movement of the finger to get the best initial angle. A mouth is thus defined between the distal end zone of the finger and the first edge surface to guide the end/edge of a sleeve-shaped bandage into the space between the handle portion, finger and connecting portion. The mouth leads into a main throat chamber 50 and the curvature of the distal end zone of the finger and that of the crown 46 of the edge 18 define outwardly flared diverging lips for the mouth 48. Within the throat, a slicing blade 52 is provided. It has a sharpened or beveled edge 54; and it is embedded between two molded plastic halves of the cutter. The blade extends across the throat from the distal end zone of the finger to the connecting portion adjacent to the juncture of the connecting portion and the handle portion.

A thickened portion 56 is provided along the first edge surface 18 of the handle portion 16 which confronts the finger 30 and serves as shield means about the sharpened edge of the cutting blade to protect the fingers and the thumb of a user in the event that, in use, they slip along the main surfaces while the cutter is being grasped by the handle portion.

Preferably, the handle portion, finger and connecting portion are of integral, molded plastic material in the rigid range, such as polypropylene, polyethylene or nylon material. The blade is preferably of stainless steel. A guide hole 57 is provided to align the blade in the plastic cutter while it is being molded. The guide hole is preferably of isosceles triangular shape with the base of the triangular hole being parallel to the sharpened edge. Preferably, the blade presents a cutting edge at a slope of between 40° and 50° to the sleeve-shaped item. Preferably, the slope is substantially 48°. It has been found that a radius of curvature of the top bearing surface along the top to cradle the index finger of a user while in use is about 2 inches, preferably.

While this invention has been shown and described in what is considered to be a preferred and practical embodiment, it is recognized that departures may be made within the spirit and scope of the invention which is not to be limited except as set forth in the following claims and within the doctrine of equivalents.

Now that the invention has been described,
What is claimed is:

1. A hand held cutter to slice a longitudinally extending opening between the ends of a generally sleeve-shaped item, such as a bandage of flexible, pliable material, while it is in position about a limb of a wearer, for easy removal by peeling open the sleeve-shaped item along the opening, said cutter comprising:

a handle portion with opposite generally planar parallel main surfaces to be gripped between the thumb and the middle finger of a user, said handle portion having a first edge surface, an opposite edge surface, a top bearing surface, and a bottom surface, the distance between said top bearing surface and said bottom surface being about 2½ inches and 3½ inches, said handle portion including a connecting portion with a top surface and a guide finger extending from the connecting portion, said finger being disposed in spaced relation along said first edge surface, said finger having a distal end zone with a terminal end, an outside surface, an inside surface confronting said first edge surface, and spaced side surfaces, said finger being symmetrical with said main faces of said handle portion and being thickened between the spaced side surfaces of said finger with respect to the thickness of said handle portion, said terminal end of said finger being spaced about 1½ inches from said top bearing surface and being about 3/16 inch to ¼ inch in thickness between said finger side surfaces, said top bearing surface and top surface of said connecting portion being symmetrical with respect to said handle portion and said top surfaces of said handle portion and top surface of said connecting portion including a thickened rim portion therealong said rim portion having side surfaces conterminous with the side surfaces of said finger, said rim portion along said top bearing surface and said top surface of said connecting portion being curved defining a cradle extending into the handle portion in a depth-wise direction generally parallel to the guide finger to accommodate a pushing force applied to the top bearing surface of the cutter by an index finger of a user, said first edge surface being curved upwardly from said bottom surface toward the terminal end of the finger to manipulate it for hooked-up engagement in the end of a sleeve-shaped item and defining a guide surface for tilting movement of the finger and defining a mouth between the distal end zone of the finger and the first edge surface to guide a sleeve-shaped item at one end into the space between the handle portion, finger and connecting portion, said space comprising a throat, said first edge surface confronting said distal end zone of said finger being curved upwardly and the inside surface of said finger along said distal end zone to said terminal end forming diverging lips of said mouth, a slicing blade with a sharpened edge embedded in the cutter and extending across the throat from the distal end zone of said finger to said connecting portion adjacent the juncture of the connecting portion and said handle portion, and said handle portion along said first edge surface confronting said finger including thickened margins comprising together with said thickened finger a guard about the sharpened edge to protect the fingers and thumb of a user.

2. The cutter as set forth in claim 1 wherein the handle portion, finger and connecting portion are integral and of molded plastic material.

3. The cutter as set forth in claim 1 wherein the blade of the cutter presents a slope of between 40° to 50° generally to the sleeve-shaped item.

4. The cutter as set forth in claim 3 wherein the slope is substantially 48°.

5. The cutter as set forth in claim 1 wherein an isosceles triangular shaped hole is provided generally midway between the opposite blade ends, the base of the hole being parallel to the sharpened edge.

6. The cutter as set forth in claim 3 wherein the handle portion, finger and connecting portion are integral and of molded plastic material.

7. The cutter as set forth in claim 1 wherein said handle portion, finger and connecting portion are of two molded and joined together halves of plastic material.

8. The cutter as set forth in claim 5 wherein said handle portion, finger and connecting portion are of two molded and joined together halves of plastic material.

9. The cutter as set forth in claim 1 wherein the bearing surface is concave and of about a radius of 2 inches.

* * * * *